(12) United States Patent
Attolino et al.

(10) Patent No.: US 9,079,856 B2
(45) Date of Patent: Jul. 14, 2015

(54) SYNTHESIS OF A GLYCOSYLTRANSFERASE INHIBITOR

(71) Applicants: Emanuele Attolino, Palagiano (IT); Andrea Malvestiti, Mapello (IT)

(72) Inventors: Emanuele Attolino, Palagiano (IT); Andrea Malvestiti, Mapello (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 0 days.

(21) Appl. No.: 14/097,398

(22) Filed: Dec. 5, 2013

(65) Prior Publication Data

US 2014/0243369 A1    Aug. 28, 2014

(30) Foreign Application Priority Data

Dec. 6, 2012 (IT) .............................. MI2012A2090

(51) Int. Cl.
*C07D 211/46* (2006.01)
*C07D 211/40* (2006.01)

(52) U.S. Cl.
CPC ............ *C07D 211/46* (2013.01); *C07D 211/40* (2013.01)

(58) Field of Classification Search
CPC .................................................... C07D 211/46
USPC .......................................... 514/315; 546/243
See application file for complete search history.

(56) References Cited

U.S. PATENT DOCUMENTS 4,639,436 A    1/1987    Junge et al.

FOREIGN PATENT DOCUMENTS

EP        0 367 748 A2    5/1990

OTHER PUBLICATIONS

Kirk-Othmer "Crystallization" Encyclopedia of chemical tecnology, p. 95-147 (2002__.*
Gaunt et al. "Rational design . . ." J. Org. Chem. 63, 4172-73 (1998).*
Berstein "Polymorphism in . . ." p. 115-119 (2002).*
Sorbera et al. "Synthesis of maglustat . . ." Prous p. 1 (2003) (from internet).*
Ellen W. Baxter et al., "Expeditious Synthesis of Azasugars by the Double Reductive Amination of Dicarbonyl Sugars", J. Org. Chem, 1994, 59, pp. 3175-3185.
Carlos R. R. Matos et al: "Synthesis of 1-Deoxynojirimycin and N-Butyl-1-deoxynojirimycin", Synthesis, vol. 1999, No. 04, Apr. 1, 1999, pp. 571-573, XP055054619, ISSN: 0039-7881, DOI: 10.1055/-1999-3430.
Miller L et al: "Solid injection, a new technique for application of insoluble samples in preparative liquid chromatography", Journal of Chromatography, Elsevier Science Publishers B.V, NL, vol. 484, Dec. 22, 1989, pp. 259-265.
Georg Schitter et al: "Synthesis of lipophilic 1-deoxygalactonojirimycin derivatives as D-galactosidase inhibitors", Beilstein Journal of Organic Chemistry, vol. 6, Mar. 1, 2010, pp. 1-7, XP055054636.
Zhen-Xing Zhang et al: "Facile and 1-9 stereo-controlled synthesis of 2-deoxynojirimycin, Miglustat and Miglitol", Tetrahedron Letters, vol. 52, No. 29, Jul. 1, 2011, pp. 3802-3804.
Search Report from the European Patent Office for IT MI 20122090 dated Feb. 28, 2013, 8 pages.

* cited by examiner

*Primary Examiner* — Celia Chang
(74) *Attorney, Agent, or Firm* — Rothwell, Figg, Ernst & Manbeck, P.C.

(57) ABSTRACT

Process for the preparation of an iminosugar, and the intermediates thereof, having known activity as a glycosyltransferase inhibitor and used, for example, in the treatment of Gaucher's disease.

5 Claims, 2 Drawing Sheets

SYNTHESIS OF A GLYCOSYLTRANSFERASE INHIBITOR

CROSS REFERENCE TO RELATED APPLICATION

Figure 1:
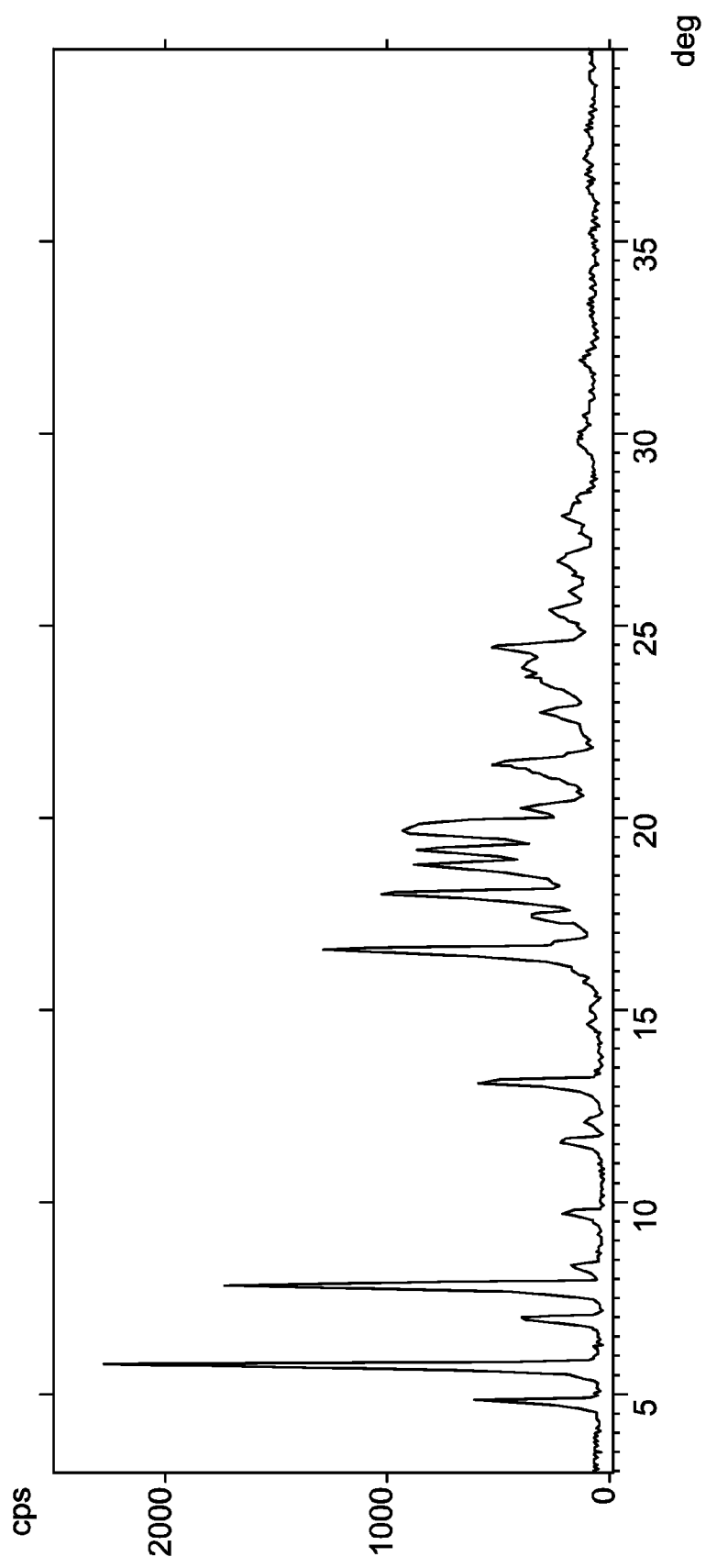

This application claims the benefit of Italian Patent Application No. MI2012A002090 filed on Dec. 6, 2012, the disclosure of which is incorporated herein in its entirety by reference.

The present invention relates to a process for the preparation of an iminosugar and the intermediates thereof, having known activity as a glycosyltransferase inhibitor and used, for example, in the treatment of Gaucher's disease.

PRIOR ART

N-butyl 1,5-dideoxy-1,5-imino-D-glucitol of formula (I), also known as N-butyl 1-deoxynojirimycin or miglustat, is a potent glycosyltransferase inhibitor, and is primarily used in the treatment of Gaucher's disease.

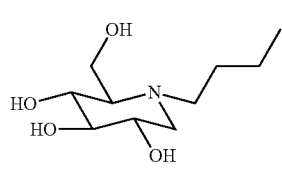

(I)

Miglustat belongs to the class of azasugars or iminosugars, compounds with multiple biological activities, characterised by the presence of a nitrogen atom on the furanose or pyranose ring of the sugar instead of an oxygen atom. The synthesis of azasugars as carbohydrate mimics began over 50 years ago. The first azasugar synthesised by Paulsen (*Chem. Ber.* 1967, 100, 802) was 1-deoxynojirimycin of formula (II), which was only isolated from natural sources years later, and demonstrated its enormous biological activity.

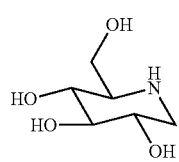

(II)

In the 1980s, a number of studies conducted on the biological activity of N-alkylated derivatives of 1-deoxynojirimycin of formula (II) demonstrated that said compounds possess a greater activity than 1-deoxynojirimycin, and the N-butyl derivative of formula (I) proved to be one of the best. As it was a synthetic derivative of 1-deoxynojirimycin, the first syntheses of miglustat were obviously conducted by introducing the butyl chain onto 1-deoxynojirimycin of formula (II) or derivatives thereof with the functional groups protected, by reductive amination with butyraldehyde (see, for example, U.S. Pat. No. 4,639,436 and EP 367748).

Said syntheses obviously shifted the synthesis problem of preparation of the N-alkylated derivative to the efficient synthesis of 1-deoxynojirimycin which, though present in nature in numerous plants and micro-organisms, cannot be extracted in sufficient amounts to allow its industrial exploitation, but must be prepared by chemical synthesis. Various methods of preparation of 1-deoxynojirimycin have been reported over the years, some of them completely chemical or biochemical with the aid of more or less complex micro-organisms, normally starting with sugars such as glucose and ribose. An interesting synthesis of N-alkylated derivatives of 1-deoxynojirimycin, including miglustat, was published by Baxter and Reitz in *J. Org. Chem.* 1994, 59, 3175-3185. This synthesis uses one of the classic methods of preparing piperidine and pyrrolidine, namely double reductive amination of 1,5-dicarbonyl derivatives with primary amines.

There are three main problems associated with development on an industrial scale of the Baxter and Reitz process, which relate to: 1) the preparation of 5-keto glucose, which involves a number of synthesis steps, the use of compounds based on tin, and low yields; 2) the stereochemistry of the reductive amination, which is selective to give the isomer with gluco stereochemistry only with some types of substituents on the hydroxyls of the starting dicarbonyl; and last but not least 3) the critical steps concerning the handling and purification of the end product, which is purified by flash chromatography.

The first two problems have been partly overcome over the years by the synthesis reported by Matos C. R. R. et al. (*Synthesis* 1999, 571-573), which uses the protected intermediate of miglustat of formula (III)

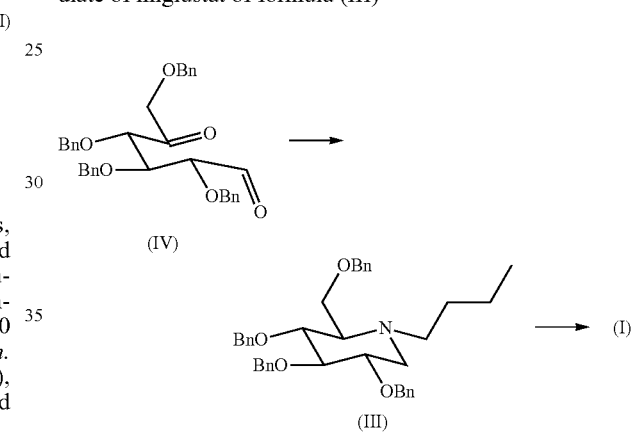

obtained from the protected dicarbonyl of formula (IV), which can be prepared without the use of tin derivatives and with good yields, starting with the commercially available 2,3,4,6-tetra-O-benzyl-D-glucitol, or by reduction of 2,3,4,6-tetra-O-benzyl-D-glucose, also commercially available, which, in turn, can be prepared from D-glucose by known methods. The intermediate of formula (III), after the debenzylation reaction, provides miglustat of formula (I).

The reductive amination reaction of a compound of formula (IV) described above was repeated in our laboratories, and the end-of-reaction crude product was analysed by HPLC.

It was thus demonstrated that in reality, reductive amination is not completely selective, and the formation of the diastereoisomer with the ido configuration of formula (V)

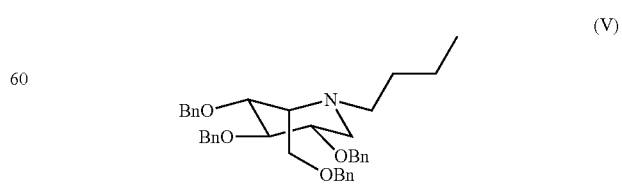

(V)

takes place together with that of the desired derivative with the gluco configuration of formula (III).

As reported by Matos C. R. R. et al., the intermediate of formula (III) is purified by flash chromatography on silica gel, and after evaporation of the fractions containing the product, a solid with a melting point of 64-65° C. is obtained.

When the process was repeated, and the resulting solid of formula (III) was analysed, it proved insufficiently pure on HPLC analysis, and the solid was amorphous, with a melting point around 64° C.

There is consequently a need for a more advantageous alternative method of preparing miglustat, and in particular its protected intermediate of formula (III). Said novel method should in particular be more industrially scalable, and therefore include an efficient method of purifying intermediate (III), not involving chromatographic purification, to obtain miglustat with a purity sufficient to allow its use in the pharmaceutical field, and at the same time provide the desired compounds with high yields.

BRIEF DESCRIPTION OF FIGURES AND ANALYSIS METHODS

N-butyl 2,3,4,6-tetra-O-benzyl-1,5-dideoxy-1,5-imino-D-glucitol of formula (III), in crystalline form, designated here as Form A, was characterised by X-ray powder diffraction (XRPD) and differential scanning calorimetry (DSC). The X-ray diffraction spectra (XRPD) were collected with the automatic diffrattometer for powders APD-2000 by Ital-Structures in the following operating conditions: Bragg-Brentano geometry, radiation CuKα (λ=1.54 Å), scanning in 3-40° in 2θ angular range with a step of 0.03° for 1 sec. The detector used is a scintillator.

The DSC traces were acquired with a Mettler-Toledo DSC 822e differential scanning calorimeter, under the following operating conditions: open aluminium capsule, range 30-400° C. at the rate of 10° C./min, with nitrogen as purge gas (80 ml/min).

The water content of N-butyl 2,3,4,6-tetra-O-benzyl-1,5-dideoxy-1,5-imino-D-glucitol in crystalline form, designated here as Form A, was determined by titration using the Karl Fisher technique.

FIG. 1: XRPD spectrum of N-butyl 2,3,4,6-tetra-O-benzyl-1,5-dideoxy-1,5-imino-D-glucitol in crystalline form, designated here as Form A; wherein the main peaks (expressed in 2θ°) are found at: 4.83, 5.76, 6.96, 7.80, 13.08, 16.50, 17.97, 18.75, 19.14, 19.62.

Figure 2:
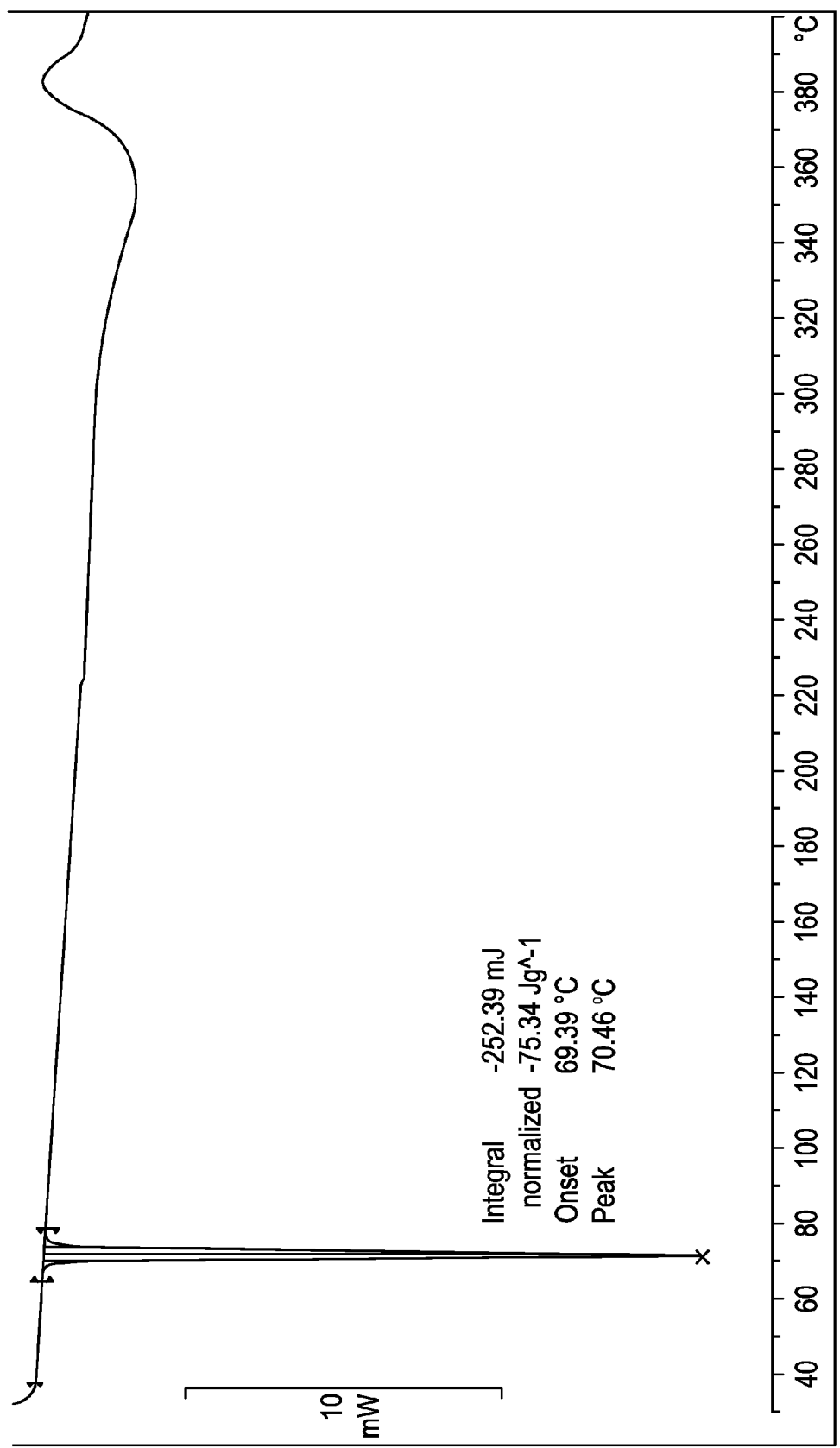

FIG. 2: DSC thermogram of N-butyl 2,3,4,6-tetra-O-benzyl-1,5-dideoxy-1,5-imino-D-glucitol in crystalline form, designated here as Form A. The endothermic peak at about 70° C. indicates the fusion process.

SUMMARY OF THE INVENTION

The first subject of the invention is a process for the purification of a compound of formula (III), namely N-butyl 2,3,4,6-tetra-O-benzyl-1,5-dideoxy-1,5-imino-D-glucitol, with high purity and in crystalline form, in particular in the form designated here as Form A. The invention also provides a process for the preparation of miglustat with high purity, comprising the use, as starting material, of a compound of formula (III) in crystalline form, in particular in crystalline form A.

DETAILED DESCRIPTION OF THE INVENTION

The first subject of the invention is a process for the purification of a compound of formula (III), namely N-butyl 2,3,4,6-tetra-O-benzyl-1,5-dideoxy-1,5-imino-D-glucitol, with high purity and in crystalline form, comprising

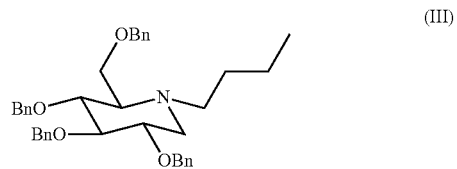

its crystallisation from a solvent medium containing a protic solvent.

According to a preferred aspect, said purification process comprises:
the dissolution of a compound of formula (III) in a solvent medium containing a protic solvent,
the formation of a precipitate; and
the recovery of the crystalline solid.

The purified product, obtainable by the purification method according to the invention, is a solid in crystalline form of N-butyl 2,3,4,6-tetra-O-benzyl-1,5-dideoxy-1,5-imino-D-glucitol, in particular in the form denominated here as Form A.

A protic solvent, in a solvent medium, can be a straight or branched $C_1$-$C_5$ alkanol, such as methanol, ethanol or isopropanol, preferably isopropanol; a carboxylic acid, such as acetic acid; water; or a mixture of two or more, typically two or three, of said solvents.

The concentration of a compound of formula (III) in the starting solution can range between about 2 and 90% w/w, preferably between about 30 and 70%.

If necessary, to promote the dissolution of the compound of formula (III), the dispersion containing said compound can be heated until complete dissolution.

The formation of the precipitate can be obtained by maintaining the solution under stirring, for example for a time ranging between about 5 and 20 hours. If necessary, to promote the formation of the precipitate the solution can be cooled, for example to a temperature ranging between about −5° and 5° C. Previously obtained crystals of crystalline form A can also be seeded to promote the formation of the precipitate.

The crystalline solid can be recovered by known techniques, such as filtration or centrifugation. In particular, if necessary, recovery can be promoted by optional addition of a solvent suitable to fluidify the dispersion, such as a $C_1$-$C_5$ alkanol, equal to or different from the one present in the solvent medium.

The solid can then be dried by known methods, for example stove-dried at a temperature ranging between about 30° C. and 55° C., under vacuum.

The crude starting material, to be subjected to the purification method according to the invention, can be a crude compound of formula (III) prepared by any of the known methods reported in the literature, for example as reported by Matos C. R. R. et al. in *Synthesis* 1999, 571-573.

A crude compound of formula (III) used as starting material therefore typically has an assay ranging between about 10 and 90% w/w, preferably between about 30% and 70% w/w.

The solid in crystalline form of a compound (III), herein denominated Form A, obtainable by the purification method according to the invention, presents an XRPD as illustrated in FIG. 1, wherein the most intense peaks (expressed in 2θ°) are found at: 4.83, 5.76, 6.96, 7.80, 13.08, 16.50, 17.97, 18.75, 19.14, 19.62. It also presents a DSC tracing as illustrated in FIG. 2, wherein the endothermic peak at about 70° C. indicates the fusion process. As said crystalline form A has a water content lower than 0.2%, preferably lower than 0.1%, it can be defined as essentially anhydrous.

A further subject of the invention is therefore a compound of formula (III), namely N-butyl 2,3,4,6-tetra-O-benzyl-1,5-dideoxy-1,5-imino-D-glucitol, in crystalline form, in particular in crystalline form A as defined above.

The dimension of the crystals of a compound (III) in crystalline form A, as obtainable by the process described above, is characterised by a $D_{50}$ value ranging between about 25 and 250 μm. If required, said value can be reduced by micronisation or fine grinding.

An end-of-reaction crude product of preparation of a compound (III), typically having an assay ranging between about 10 and 90% w/w, preferably between about 30% and 70% w/w, can then be subjected to the purification process according to the invention to obtain its crystalline form, in particular crystalline form A, with a chemical purity evaluated by HPLC greater than or equal to 95%, preferably greater than or equal to 98%.

In particular, a compound of formula (III) in crystalline form, in particular in Form A, obtained by the process according to the invention, presents a content of a compound in the ido configuration of formula (V)

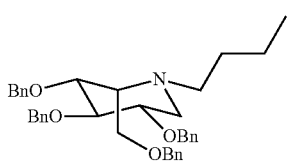

(V)

in quantities lower than 0.2%, preferably lower than 0.1%, calculated by HPLC.

A compound of formula (III), in crystalline form, in particular in crystalline form A, thus obtained, can be subjected to a debenzylation reaction to obtain miglustat with a high yield and purity.

The debenzylation reaction can be conducted according to known methods by removing the benzyl protecting group from the hydroxyl functions, preferably by catalytic hydrogenation.

A further subject of the present invention is therefore a method of preparing miglustat of formula (I)

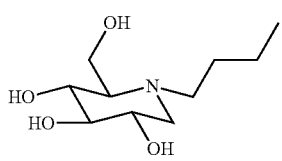

(I)

comprising the use as starting material of a compound of formula (III) in crystalline form, in particular in crystalline form A.

Miglustat thus obtained has a chemical purity greater than or equal to 98%, more preferably greater than or equal to 99%.

In particular, the miglustat product, as API (active pharmaceutical ingredient), obtained by the process according to the invention, presents a content of a compound in the ido configuration of formula (V)

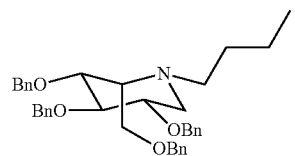

(V)

in quantities lower than 0.1%, preferably lower than 0.05%, calculated by HPLC.

A further subject of the invention is a pharmaceutical composition containing miglustat as active ingredient, a compound in the ido configuration of formula (V)

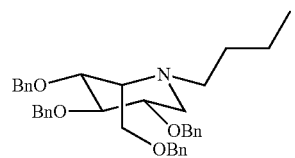

(V)

in quantities lower than 0.1%, preferably lower than 0.05%, calculated by HPLC, and a carrier and/or a pharmaceutically acceptable diluent.

The dimension of the miglustat crystals, as obtainable by the process described above, is characterised by a $D_{50}$ value ranging between about 25 and 250 μm. If required, said value can be reduced by micronisation or fine grinding.

The following examples illustrate the invention.

Example 1

Synthesis of N-butyl 2,3,4,6-tetra-O-benzyl-1,5-dideoxy-1,5-imino-D-glucitol (III)

A solution of oxalyl chloride (99.8 g, 0.79 mol) in dichloromethane (300 ml) is cooled to −75° C., treated under inert atmosphere in sequence with a solution of DMSO (77.1 g, 0.99 mol) in dichloromethane (100 ml) added by slow dripping, and then, after about 1 h, with a solution obtained by dissolving 2,3,4,6-tetra-O-benzyl-D-glucitol, prepared as in *Synthesis* 1999, 571-573 (HPLC assay 94.5%, 105.9 g, 0.18 mol) in dichloromethane (100 ml), added by slow dripping. The reaction mixture is maintained under stirring at a temperature not exceeding −65° C., and treated after about 2 hours with triethylamine (187 g, 1.85 mol), added by slow dripping, maintaining the reaction mixture under stirring at a temperature not exceeding −50° C. for at least 4 hours. The end-of-reaction mixture is then added to a mixture maintained under stirring under inert atmosphere at the temperature of 0° C., obtained by mixing n-butylamine (135 g, 1.84 mol), acetic acid (111 g 1.85 mol), sodium sulfate (32.5 g, 0.51 mol) and sodium cyanoborohydride (31.7 g, 0.48 mol) in methanol (400 ml).

The pH of the reaction mixture thus obtained is corrected by adding further acetic acid until a value of pH 6 is obtained, and the mixture is maintained under stirring at about 20° C. for 15 hours. The end-of-reaction mixture is then treated in sequence with a 20% aqueous solution of NaOH, 3M HCl to pH 6, an 11% solution of NaClO, a 10% solution of $Na_2SO_3$, a saturated solution of $NaHCO_3$, and finally with neutral water. The organic phase thus obtained is dried on anhydrous $Na_2SO_4$, filtered and concentrated at low pressure, to obtain an oily residue weighing about 120 g. The crude product thus obtained, analysed by HPLC, presents a ratio of about 4:1 between the product of formula (III) and the product of formula (V).

Example 2

Crystallisation of N-butyl 2,3,4,6-tetra-O-benzyl-1,5-dideoxy-1,5-imino-D-glucitol (III)

The crude compound of formula (III), obtained as in Example 1, is dissolved in isopropanol (120 ml), and the resulting solution is cooled in an ice bath and treated with water (18 ml). The suspension obtained is maintained under stiffing at about 20° C. for 15 hours, and then filtered through a Buchner funnel and the panel washed with isopropanol. The wet solid is stove-dried at the temperature of 50° C., under vacuum, to a constant weight, supplying 50 g of compound of formula (III) with high chemical purity, in crystalline form A, wherein the main peaks (expressed in 2θ°) are found at: 4.83, 5.76, 6.96, 7.80, 13.08, 16.50, 17.97, 18.75, 19.14 and 19.62. Said crystalline product presents a DSC tracing as illustrated in FIG. 2, and a water content below 0.1%.

The compound of formula (III) can be recrystallised from isopropanol alone to obtain a compound of formula (III) with a purity, calculated by HPLC, exceeding 99%.

Example 3

Synthesis of Miglustat of Formula (I)

A solution obtained by mixing N-butyl 2,3,4,6-tetra-O-benzyl-1,5-dideoxy-1,5-imino-D-glucitol of formula (III), obtained as in Example 2 (105.1 g, 0.17 mol) in methanol (500 ml) in the presence of 32% HCl (43.5 g). is treated with 16% Pd/C (10.2 g). The mixture is maintained under vigorous stirring under hydrogen atmosphere at 4 bars for about 4 hours, and then filtered through a perlite panel, and the solution obtained is concentrated at low pressure. The solid residue thus obtained is dissolved in water (100 ml), and the resulting acid solution is passed through a column on an ion-exchange resin activated in basic form (Amberlite IRA 900Cl). The fractions that tested positive to the ninhydrin assay were combined and concentrated at low pressure, obtaining 50 g of miglustat as an oily residue, having a chemical purity exceeding 98%, calculated by HPLC.

Example 4

Crystallisation of Miglustat of Formula (I)

200 g of miglustat of formula (I) obtained as in Example 3 is diluted in methanol and treated by slow dripping, under stirring at about 20° C., with acetone. The suspension formed is maintained under stirring at the same temperature for 5 hours and then filtered through a Buchner funnel, and the solid obtained is washed with acetone and dried at 50° C. under vacuum to a constant weight. 131 g of miglustat is obtained, with a purity calculated by HPLC exceeding 99.5%.

The invention claimed is:

1. A compound of formula (III), namely N-butyl 2,3,4,6-tetra-O-benzyl-1,5-dideoxy-1,5-imino-D-glucitol,

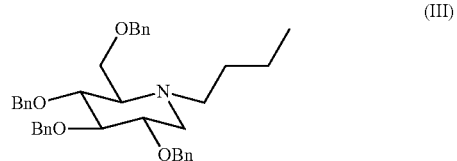 [SMILES: CCCCN1CC(OCc2ccccc2)C(OCc2ccccc2)C(OCc2ccccc2)C1COCc1ccccc1]

in crystalline Form A, having an XRPD spectrum as shown in FIG. 1, wherein the most intense peaks (expressed in 2θ) are to be found at: 4.83, 5.76, 6.96, 7.80, 13.08, 16.50, 17.97, 18.75, 19.14, and 19.62.

2. The compound according to claim 1, wherein the content of a compound in the ido configuration of formula (V)

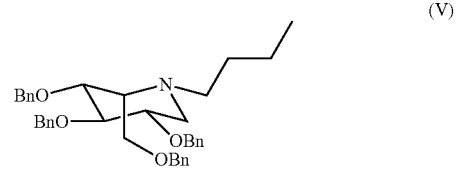 [SMILES: CCCCN1CC(OCc2ccccc2)C(OCc2ccccc2)C(OCc2ccccc2)C1COCc1ccccc1]

is less than 0.2% as determined by HPLC.

3. The compound according to claim 2, wherein the content of a compound in the ido configuration of formula (V) is less than 0.1% as determined by HPLC.

4. A method for preparing miglustat of formula (I),

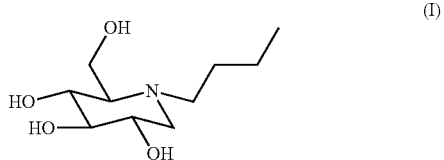

comprising debenzylating a compound of formula (III) in crystalline Form A, as defined in claim 1.

5. The method of claim 4, wherein the debenzylating occurs by catalytic hydrogenation.

* * * * *